(12) United States Patent
Luoma, II et al.

(10) Patent No.: US 6,588,625 B2
(45) Date of Patent: Jul. 8, 2003

(54) SAMPLE HANDLING SYSTEM

(75) Inventors: Robert P. Luoma, II, Highland, TX (US); David C. Arnquist, The Colony, TX (US); James D. Hause, Grapevine, TX (US)

(73) Assignee: Abbott Laboratories, Abbott Park, IL (US)

( * ) Notice: Subject to any disclaimer, the term of this patent is extended or adjusted under 35 U.S.C. 154(b) by 80 days.

(21) Appl. No.: 09/840,960

(22) Filed: Apr. 24, 2001

(65) Prior Publication Data
US 2002/0169518 A1 Nov. 14, 2002

(51) Int. Cl.$^7$ ................................................ G07F 11/00
(52) U.S. Cl. ............................................ 221/9; 422/64
(58) Field of Search ............................ 221/2, 3, 7, 13, 221/1, 9; 700/231, 236, 241; 422/64, 65, 67; 436/47, 48, 50

(56) References Cited

U.S. PATENT DOCUMENTS

| | | |
|---|---|---|
| 3,832,135 A | 8/1974 | Drozdowski et al. |
| 3,985,507 A | 10/1976 | Litz et al. |
| 4,077,444 A | 3/1978 | Gilson et al. |
| RE30,627 E | 5/1981 | Bagshawe et al. |
| 4,276,258 A | 6/1981 | Ginsberg et al. |
| 4,299,796 A | 11/1981 | Hogen Esch |
| 4,363,782 A | 12/1982 | Yamashita |
| 4,501,164 A | 2/1985 | Stockdale et al. |
| 4,582,990 A | 4/1986 | Stevens |
| 4,676,951 A | 6/1987 | Armes et al. |
| 4,678,752 A | 7/1987 | Thorne et al. |
| 4,774,055 A | 9/1988 | Wakatake et al. |
| 4,844,868 A | 7/1989 | Bokugawa |
| 4,906,432 A | 3/1990 | Geiselman |
| 4,931,402 A | 6/1990 | Abplanalp |
| 4,965,049 A | 10/1990 | Lillig et al. |
| 5,071,625 A | 12/1991 | Kelln et al. |
| 5,087,423 A | 2/1992 | Ishibashi |
| 5,122,342 A | 6/1992 | McCulloch et al. |
| 5,163,802 A | 11/1992 | Poinelli |
| 5,244,633 A | 9/1993 | Jakubowicz et al. |
| 5,260,872 A | * 11/1993 | Copeland et al. ............. 422/65 |
| 5,314,825 A | 5/1994 | Weyrauch et al. |
| 5,380,487 A | 1/1995 | Choperena et al. |
| 5,483,843 A | 1/1996 | Miller et al. |
| 5,575,976 A | 11/1996 | Choperena et al. |
| 5,591,642 A | 1/1997 | Jones |
| 5,601,783 A | 2/1997 | Breeser et al. |
| 5,658,799 A | 8/1997 | Choperena et al. |
| 5,665,309 A | * 9/1997 | Champseix et al. ........ 141/130 |
| 5,681,530 A | 10/1997 | Kuster et al. |
| 5,693,292 A | 12/1997 | Choperena et al. |
| 5,736,102 A | 4/1998 | Seaton et al. |
| 5,853,667 A | 12/1998 | Seaton et al. |
| 5,876,670 A | 3/1999 | Mitsumaki et al. |
| 5,882,596 A | 3/1999 | Breeser et al. |
| 5,972,295 A | * 10/1999 | Hanawa et al. ............... 422/63 |
| 6,056,921 A | 5/2000 | Rao et al. |
| 6,071,477 A | 6/2000 | Auclair et al. |

FOREIGN PATENT DOCUMENTS

| | | | |
|---|---|---|---|
| EP | 0867724 A2 | * | 9/1998 |
| EP | 0809112 A2 | * | 2/2000 |
| EP | 0979999 A2 | * | 2/2000 |
| JP | 62098262 | * | 5/1987 |
| JP | 03183957 | * | 8/1991 |
| JP | 04172252 | * | 6/1992 |
| JP | 06034642 | * | 2/1994 |
| JP | 2000046842 | * | 2/2000 |

* cited by examiner

Primary Examiner—Kenneth W. Noland
(74) Attorney, Agent, or Firm—Beth A. Vrioni (57) ABSTRACT

A sample handling system includes a loading rack for receiving carriers with a plurality of test tubes holding samples. A robotic device transports a carrier with the samples to a positioner that moves the tubes within the carrier into an aspiration position. After aspiration, the robotic device returns the carrier to the loading rack. The system provides for handling of stat samples and automatic retesting of samples.

20 Claims, 6 Drawing Sheets

SAMPLE HANDLING SYSTEM

FIELD OF THE INVENTION

The present invention relates to a sample handling system for automatically testing samples with a diagnostic module. More particularly, the invention relates to a sample handling system that includes a robotic arm for moving a carrier with a plurality of sample tubes from a loading rack to a predetermined location to be tested by a diagnostic analyzer and then returning the carrier to the loading rack for unloading or retesting.

BACKGROUND OF THE INVENTION

In the past, sample handling systems had a single path carrier that would stop at specified locations as desired for testing. In these single path systems, if retesting or preemptive prioritization of a sample were required, the tube would have to travel around the entire module system to be tested or retested. This resulted in either significant delay in testing and retesting or very complex expensive carrier routing mechanisms.

An example of a single path sample handling device is disclosed in U.S. Pat. No. 5,876,670 to Mitsumaki. In Mitsumaki, a sample carrier, holding a plurality of test tubes, is transferred to the analyzer modules by a transporting belt driven by a motor. All the sample carriers on the transporting belt pass through the sampling position for the first analyzer module and must be transferred to a receiving position to reach the sampling position for the second analyzer module. When a sample needs to be retested, then the operator returns the sample carrier to the beginning of the transporting belt. An urgent sample supply portion is provided on one end of the belt near the sample supply portion, allowing urgent sample racks to be processed before the general racks. In Mitsumaki, the sample handling system processes samples sequentially along the transporting belt and does not automatically retest samples.

Another example of a prior sample handling system is disclosed in U.S. Pat. No. 5,665,309 to Champseix et al. The Champseix et al. device comprises a holding rack for a plurality of test tubes; a sampling station for sampling the contents of a tube; and a gripping device for withdrawing a tube from a selected position on the rack, bringing the tube to the sampling station and returning the tube back to its selected position. The gripping device moves the individual tubes from a rack to the sampling station. However, the Champseix et al., sample handling device does not disclose a method for automatically retesting samples or processing stat samples.

U.S. Pat. No. 5,260,872 to Copeland discloses an automated testing system for the quality testing of production samples, comprising a loading station for receiving a test tube rack containing a plurality of test tubes; a pipetting station; a bead-drop station; and a robotic device having an arm adapted to pick up a test tube rack from the loading station, move the rack to the pipetting station so the fluids can be pipetted into the test tubes; move the rack to the bead-drop station; and return the rack to the loading station in accordance with a computer program. When the Copeland test tube rack is returned to the loading station the tubes may be removed and disposed of and the rack is then loaded with a fresh set of test tubes. The Copeland system does not accommodate for automatic retesting or testing of stat samples.

SUMMARY OF THE INVENTION

The present invention is a random sample handling system for moving samples to and from a diagnostic module for automatic testing and retesting. The random handling system includes a loading rack for receiving a plurality of carriers. The carriers can include several tubes filled with samples. In a preferred embodiment, the sample carriers are arranged in a stationary linear array on a loading rack positioned in front of the diagnostic modules. The operator may load the carriers individually or in trays for convenient handling of multiple carriers. Individual carrier slots are provided for loading high priority or stat samples that require immediate processing.

A robotic device is provided to transport the carriers to and from the loading rack and to and from a carrier positioner adjacent the diagnostic module(s). The robotic device has an arm, which is controlled by a programmable computer, moving the carriers as required for testing and retesting. The system includes software that allows users to flexibly configure rules or criteria for retesting samples. These rules can also be utilized to change to another type of test depending on the results of a previous test. This can be a very cost effective approach that when utilized minimizes operator involvement in real time. The system also includes a software capability that can suspend the operation of the sampler handler in the event the user decides to change the test request(s) for a particular sample after loading the carrier.

The carrier positioner is located adjacent a diagnostic module for positioning the carriers so the samples selected for testing can be aspirated by a probe. The positioner includes a carriage connected to a lead screw driven by a stepping motor in response to commands from the programmable computer. In a preferred embodiment, the carrier positioner can accommodate at least two carriers, allowing the processing module to test one carrier while the transporter loads another carrier onto the positioner to maintain the system throughput.

A barcode reader is provided to read carrier and sample identification. A bar code reader in the system reads bar coded labels attached to the carriers and the sample tubes as the robotic device passes the carriers by the reader.

Only one robotic device and barcode reader are required for the present system, regardless of size. The invention can be dynamically configured for variable queue sizing depending on the user's particular workload. Additionally, the total capacity of the system can be changed based on peak loading requirements that vary across testing segments in the laboratory.

In operation, the robotic arm picks up a carrier from the loading rack and travels past the bar code reader to identify the carrier and samples. Tests previously programmed in the computer are assigned to each tube in the carrier. The robotic arm delivers the carrier to be tested to the carrier positioner. The positioner is controlled by the computer to move the carrier to a predetermined location adjacent a pipetter on the diagnostic module. The pipetter aspirates samples from the tube for testing. When the tests are completed on all the tubes in the carrier, the robotic arm loads the carrier and returns the carrier to its designated location in the loading rack. While the tubes of one carrier are being aspirated, a second carrier can be moved to the carriage.

The sample handling system can include more than one diagnostic module. For example in one preferred embodiment, the sample handling system includes two diagnostic modules, a clinical chemistry test module and an immunoassay module. A carrier positioner is provided for each diagnostic module in the system.

An object of the present invention is to provide a modular random sampling system that can be adapted to a variety of diagnostic modules. The present sample handling system is modular and scalable to different sizes of processing modules and may be used for single or multiple module systems. The system provides random access to sample carriers on the loading rack. This random access capability allows the system to access and process high priority samples rapidly. This capability also allows the system to balance the workload of multiple processing modules with different throughput capabilities. After samples are processed initially, the sample carriers are returned to their slots in the loading area and then accessed again when the initial testing is complete to provide automated retest capability. This automated retest capability does not require any additional intervention by the operator. Random access assures the samples to be retested can be processed in the shortest possible time. The system is mechanically simple, which minimizes system cost and maximizes system reliability. The present system is self-contained and can be assembled and tested independently of the processing modules for ease of manufacture and installation in the field.

Another object of the present invention is to provide a system that processes samples for testing and retesting in a faster time and with more reliability than previous handling systems. Additionally, an object of the present invention is to provide a sample handling system that provides faster processing of high priority samples while maintaining throughput of routine test samples.

A further object of the present invention is to provide a system having a robotic means for moving a carrier with a plurality of test samples from a loading rack to a sample testing area and returning the carrier to the loading rack and having a programmable computer for (1) controlling the robotic means, (2) selecting carriers for testing based on predetermined priority, (3) achieving positive identification of the carriers and samples, and (4) identifying a breach of positive identification when an access door has been opened or a carrier has been removed prematurely.

Additional advantages of the invention will be realized and attained by the apparatus and method particularly pointed out in the written description and claims hereof, as well as from the appended drawings. It is to be understood that both the foregoing general description and the following detailed description are exemplary and are intended to provide further explanation of the invention claimed.

DETAILED DESCRIPTION

Figure 1:
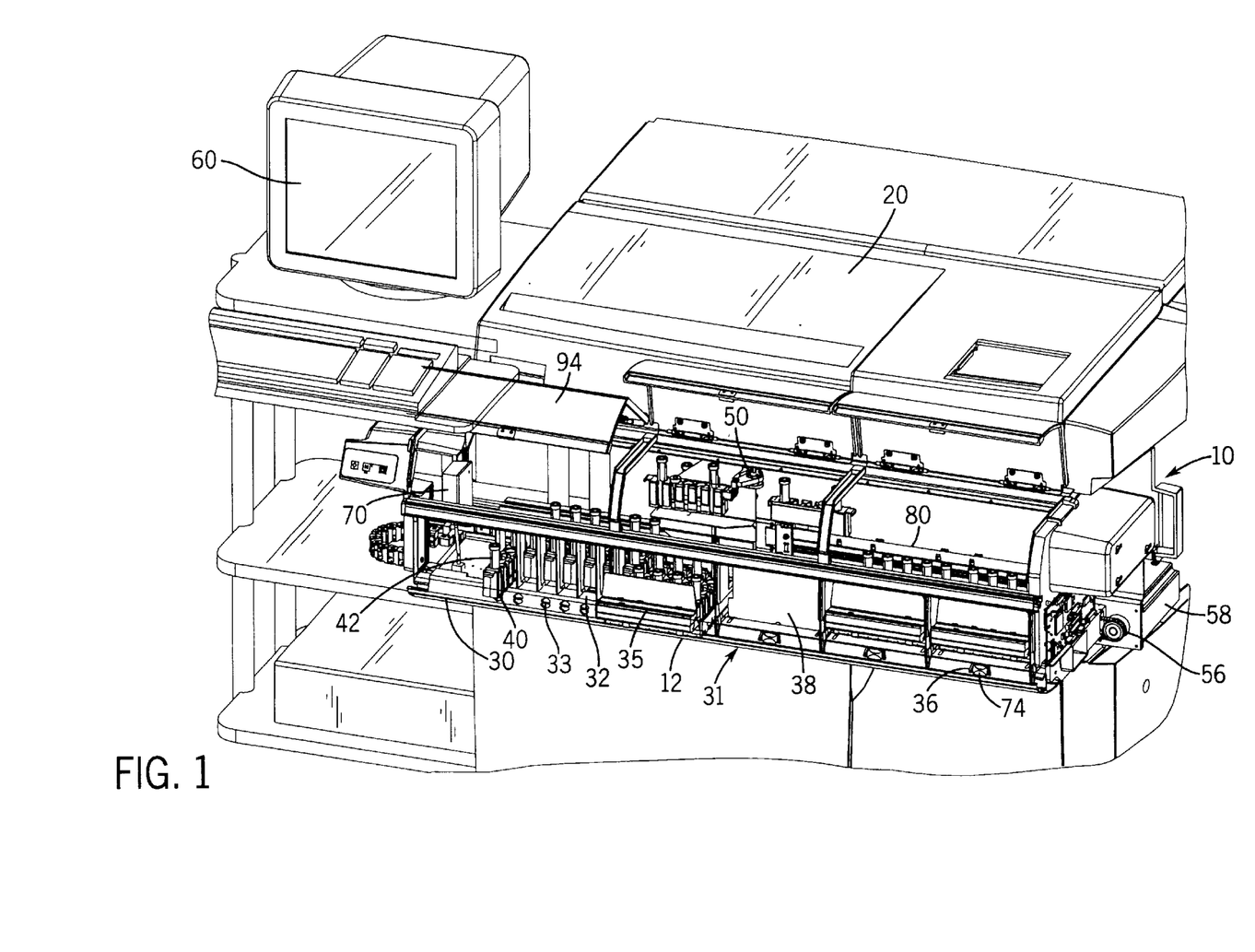
FIG. 1 is a perspective view of a preferred embodiment of the sample handling system of the present invention.
Figure 2:
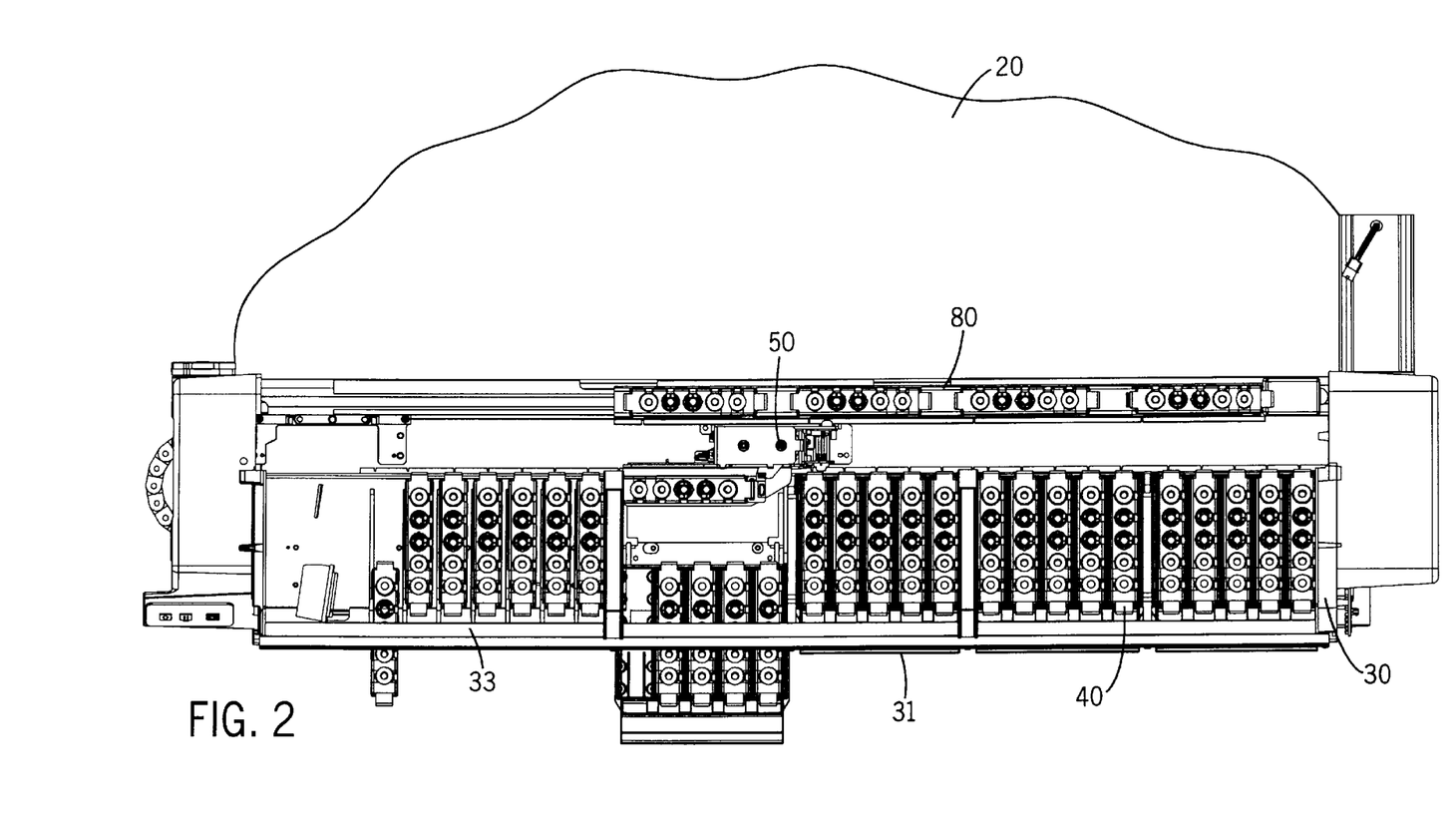
FIG. 2 is a top plan view of the sample handling system of FIG. 1 with access doors removed.

The present invention is a sample handling system, generally designated by the numeral 10. As shown in FIGS. 1 and 2, the present sample handling system 10 includes a loading rack 30 with a plurality of slots 32 for receiving a plurality of carriers 40. Each carrier 40 can hold a plurality of containers 42, such as tubes or cups, filled with samples. In this example, each carrier 40 can hold five tubes 42. However, the carriers 40 can be configured to hold either more or less tubes 42 depending on the system requirements.

The sample carriers 40 are arranged on the loading rack 30 in a stationary linear array near the processing modules 20. The operator can load the carriers 40 onto the loading rack or platform 30 individually into slots 32 or in trays 35 for convenient handling of multiple carriers. The loading rack 30 can be configured in different shapes such as circular with slots aligned around the circular tray. The loading rack 30 includes a routine loading area 31 and an urgent or stat sample area 33. In a preferred embodiment of the present invention, the routine loading area 31 comprises a plurality of bays 36, each bay 36 accommodating a tray 35. Each bay 36 includes a door 38 attached to the loading rack 30. Each door 38 includes a latch 39 that is automatically released by insertion of a tray 35. This latch 39 is difficult to actuate by hand to prevent an operator from affecting the operation of the carriers 40.

The carriers 40 may be loaded onto a tray 35 before loading the tray 35 into the loading rack 30 from the front 12 of the handling system 10. Alternatively, a carrier can be loaded onto the tray previously loaded onto the loading rack 30. In this example, a tray 35 accommodates up to five carriers and the loading rack accommodates seven stat carriers 40 and four routine trays 35 holding up to 25 samples each. However, the loading rack 30 may be configured differently to accommodate peak loading requirements that vary across testing segments in the laboratory.

The carriers 40 are positioned in the tray slots until selected for testing or retesting. A carrier 40 is released for unloading immediately after retest or after all tests in the carrier 40 are complete and no retests are required. A tray 35 is released for unloading when all the carriers 40 in the tray 35 are released for unloading. A high priority or stat carrier 40 is loaded into the high priority sample area 33. A carrier 40 located in the high priority area 33 is transferred to the carrier positioner 80 for aspiration and then is returned to the stat area 33 until a programmable computer 60 determines if a retest is needed. A stat carrier 40 is released for unloading after all tests are completed and any retest requests are aspirated.

A plurality of status indicators 74 are provided to indicate to the operator when a completed tray 35 or an individual carrier 40 in the high priority area 33 may be removed. For example, the status indicator light 74 is green to indicate the corresponding tray 35 or carrier 40 can be accessed or the status indicator light 74 is amber to indicate the tray 35 or carrier 40 is in process and should be left in place until completed.

The present sample handling system 10 includes a means for detecting that a new tray 35 or new carrier 40 in the high priority area has been loaded. A loading rack sensor 98 (not shown) is located in each bay or stat slot to detect the presence of a tray or carrier respectively. If a new tray is detected the contents of the tray 35 are scanned by a first sensor 102 on the carrier transporter 50 to determine if any carriers are in the tray.

Figure 6:
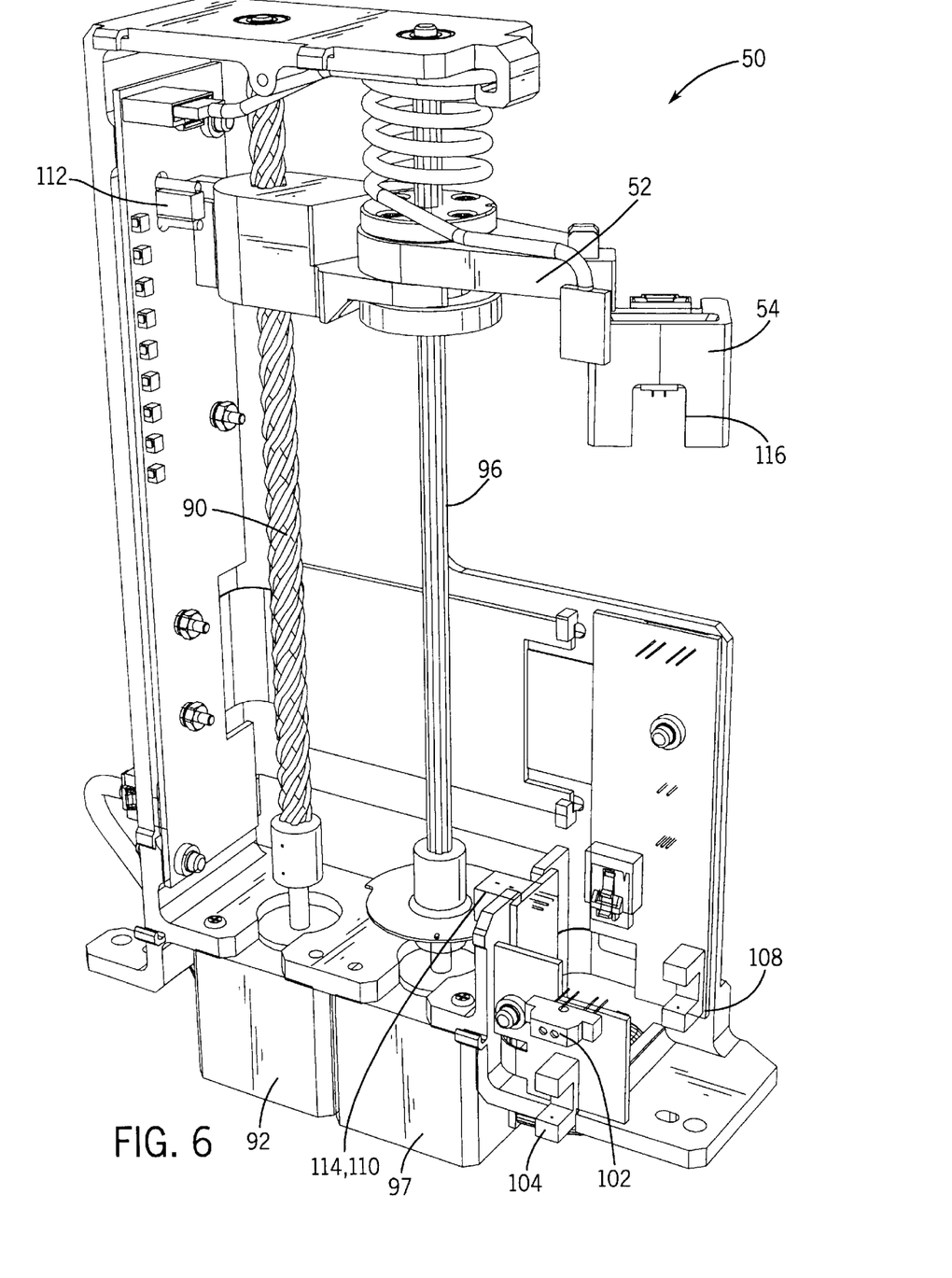
FIG. 6 is a perspective view of a preferred embodiment of a transporter.

In a preferred embodiment, the sample handling system 10 includes a carrier transporter 50 that consists of a robotic device having a robotic arm 52 to move the carriers 40 as required for testing and retesting (see FIG. 6). The robotic arm 52 has a gripper device 54 that picks up the carrier 40 by a support tab 48. The robotic transporter 50 includes a drive motor 58 that is controlled by a programmable computer 60. In the preferred embodiment, the robotic arm 52 traverses the length of the loading platform 30 by a timing belt 56. However, it is understood by a person skilled in this art that other means can be used to move the robotic arm 52.

The transporter 50 is capable of lifting a carrier 40 a height just slightly more than the total height of the carrier 40 holding a tube 42 in the loading rack 30. The vertical motion of the transporter 50 is created by a lead screw 90 driven by a stepping motor 92. The robot transporter 50 can also rotate a carrier 40 through a 180 degree range of motion between positions for barcode reading, access to carrier slots and access to a carrier positioner 80. The rotational motion of the transporter 50 is provided by a spline shaft 96 coupled to a stepping motor 97. The spline shaft 96 allows the robotic arm 52 to move vertically while maintaining accurate angular positioning. Although the preferred embodiment includes specific means to move the robotic transporter, it is understood by a person skilled in this art that other means could be used to move the transporter 50.

Figure 5:
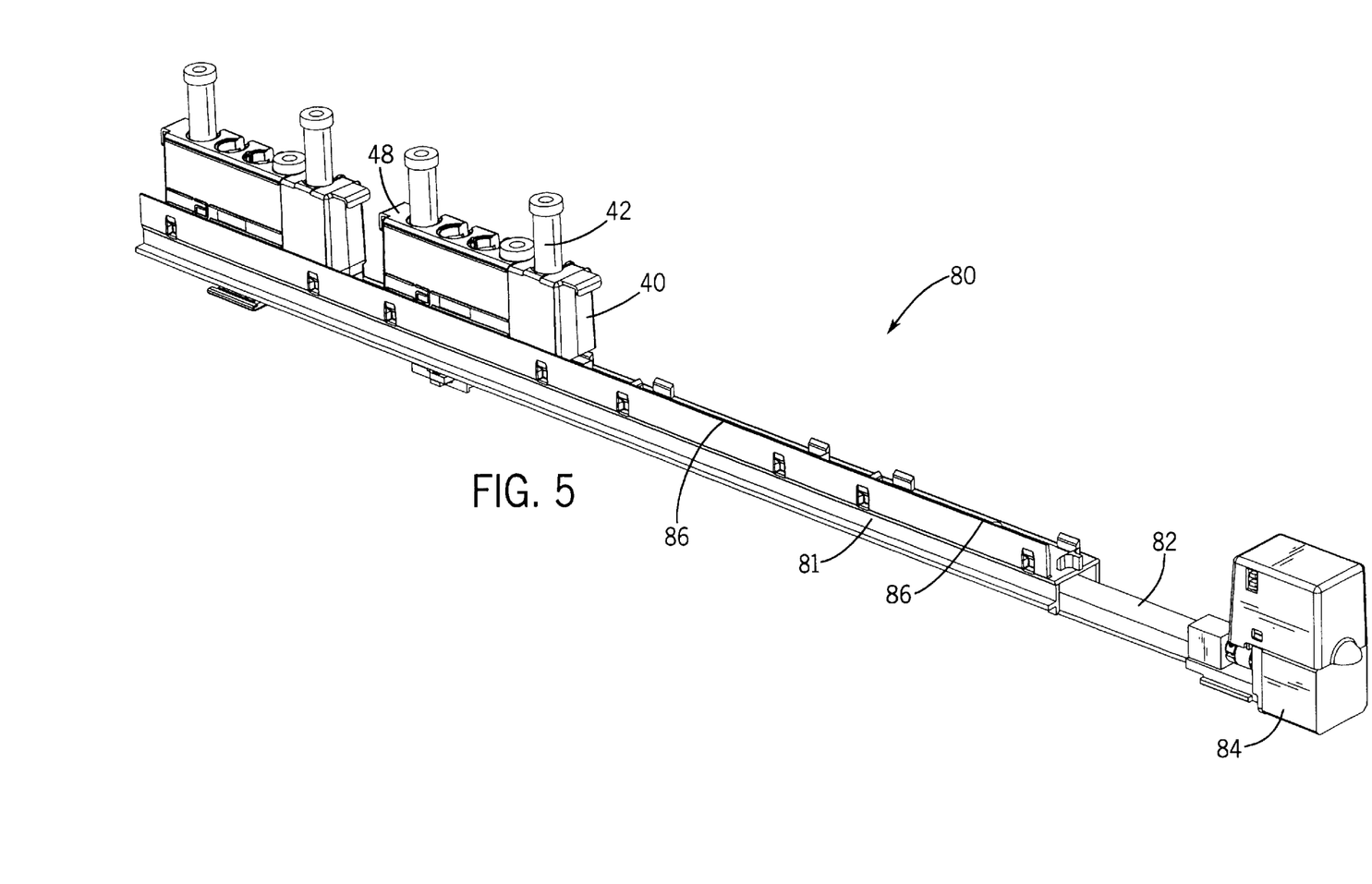
FIG. 5 is a perspective view of a preferred embodiment of a carrier positioner.

The present sample handling system 10 also includes a carrier positioner 80 located adjacent a diagnostic module 20 for conducting tests on the samples in the test tubes 42 (see FIG. 5). In the preferred embodiment, the carrier positioner 80 has a plurality of openings 86 for receiving carriers. The positioner 80 can position at least two complete carriers underneath the testing point(s) of a processing module, allowing the processing module to aspirate from one carrier 40 while the transporter 50 loads another carrier 40 on the positioner 80 to maintain system throughput. The carrier positioner 80 includes a carriage 81 on a lead screw 82 driven by a stepping motor 84 in response to commands of the computer 60. Although in the preferred embodiment the positioner 80 is driven by a lead screw 88, the positioner 80 could be driven by other known driving means such as a belt, a chain, an air cylinder, or a linear motor. The positioner 80 may be a variety of configurations, including having multiple openings 86 for routine carriers and high priority carriers.

In a preferred embodiment, the carrier positioner 80 has four openings 86 to accommodate the needs of several different types of processing modules using common hardware to reduce the overall product cost of the system (see FIG. 5). The positioner 80 is configured to adapt to a variety of diagnostic modules 20. For example, two openings may be used for one pipetter and the other two openings for a different pipetter in the same diagnostic module 20. Alternatively, two openings may accommodate solely high priority sample carriers while the other two openings accommodate routine sample carriers.

The robot transporter 50 executes the following six basic carrier handling operations: 1) pick up carrier 40 from loading rack 30; 2) place carrier 40 into loading rack 30; 3) place carrier 40 onto positioner 80; 4) pick up carrier 40 from positioner 80; 5) present carrier 40 to a barcode reader 70; and 6) scan trays 35 for carriers 40.

In a preferred embodiment of the present invention, the robot transporter 50 includes nine sensors for monitoring the correct operation of the system. Due to the unique value and hazards of the biological samples being transported, a high degree of capability to monitor and verify the operation of the transporter 50 is important. A first reflective sensor 102 on the transporter 50 is used to determine the presence of a carrier 40 in a tray 35 or slot 32. A second (carrier slot alignment) sensor 104 is used to verify correct alignment between the transporter 50 and the carrier slots on the loading rack for pick up and placement of the carriers. A third (carrier positioner alignment) sensor 106 is used to verify alignment between the transporter and the openings 86 in the positioner 80. A fourth reflective sensor 107 is used to determine if a carrier 40 is present on the positioner 80. The horizontal, rotational, and vertical motions of the transporter 50 are monitored by fifth, sixth, and seventh sensors 108, 110 and 112 respectively. An eighth sensor 114, positioned with the rotational motion sensor 110, is used to verify the correct rotational position of the robotic arm 52. Located on the robotic arm 52 is a ninth sensor 116 used to verify that the carrier 40 is properly engaged in the arm 52 for safe transport. Although the preferred embodiment includes the above-described nine sensors, it is understood by a person skilled in this art that other means could be used to monitor and verify the operation of the transporter 50 and the robotic arm 52.

A bar code reader 70 is included in the present sample handling system to read carrier and sample identification. Bar coded labels 72 are attached to the carriers 40 and, optionally on the sample tubes 42. The carrier 40 is scanned once with a barcode reader 70 when the carrier 40 is first selected. After being scanned, the carrier 40 is moved by only the transporter 50 or the linear positioner 80. At this point, all motions of the carrier 40 generate position and alignment feedback to the computer 60, so the carrier identification only needs to be read by the barcode reader 70 once.

Many types of diagnostic modules 20 can be employed with the present random sampling handling system 10, including immunoassay modules or clinical chemistry test modules. Examples of suitable diagnostic modules include ARCHITECT® i1000, i2000, and c8000 processing modules, manufactured by Abbott Laboratories, Abbott Park, Ill.

In a preferred embodiment of the sample handling system 10 a plurality of access covers 94 are positioned over the loading rack 30. When an access door 94 is opened, an interlock (not shown) connected to the access cover 94 will indicate a breach of positive identification, requiring the barcode reader 70 to rescan the carriers 40.

During operation of the present sample handling system 10, an operator loads the trays 30 or individual carriers 40 onto the loading rack 30. Either the operator inputs into the computer the patient sample identification and the test orders or this information may be downloaded into the computer 60 from a lab information system. A test order may require a plurality of separate assays. Once a sample is loaded, the programmable computer 60 determines the order of the different sample tests based on a preprogrammed priority. The system detects the presence of the carriers 40 and selects one for sampling. The computer 60 activates the robotic transporter 50 to pick up the selected carrier 40 from the loading rack 30 and transport the carrier 40 past the bar code reader 70 to identify the carrier 40 and the sample tubes 42, the bar code data is sent to the programmable computer 60. Tests previously programmed in the computer 60 are assigned to each tube 42 in the carrier 40. The transporter 50 then delivers the carrier 40 to the positioner 80. Software in the computer 60 controls the movement of the positioner 80, moving the carrier 40 to a predetermined location adjacent a testing site or pipetter on the diagnostic module 20. The pipetter withdraws the sample from a tube 42 for testing.

When the tests are completed on all the tubes 42 in the carrier 40, the robotic arm 52 loads the carrier 40 and then moves and returns the carrier 40 to its assigned location on the loading rack 30. While the tubes 42 of one carrier 40 are being aspirated, a second carrier 40 can be loaded onto the carriage 80 for testing. At this point, the status indicator 74 will show a hold status for the carrier 40 until the computer 60 makes the retest decision. If a retest is needed, the carrier 40 will be selected again with the same process described above, but without a bar code scan. The robot 50 continues to pick up carriers 40, scan and place the carriers 40 as required. The status indicator 74 at each tray 35 or slot 32 will show a completed tray of carriers 35 or carrier 40 when retesting is not required. The operator should remove the completed carrier 40 or tray of carriers 35 when they have been released for unloading.

Positive identification of the carriers is violated if an access cover 94 of the sample handling system 10 is opened. When an access door 94 is opened all carriers 40 must be rescanned before further testing to provide positive identification. Further, positive identification of a carrier 40 is violated if a carrier 40 or a tray 35 on the loading rack 30 is removed prematurely. At this point the carrier 40 or tray 35 that was removed prematurely must be replaced and rescanned. Slot and tray sensors 98 are monitored continuously to identify such violation of the positive identification. The programmable computer 60 rapidly checks the status of each individual tray or carrier sensor 98 in sequence. If a change in sensor state is observed, the computer 60 can determine that a carrier 40 or tray 35 has been removed and the identity of the contents can no longer be assured until the carriers 40 in question are re-scanned.

In the preferred embodiment, the robot arm 52 cannot access the linear positioner 80 while it is moving. For example, if the positioner 80 accommodates two carriers 40, and two carriers 40 are already on the positioner 80, no preemption is allowed for a high priority or stat sample. The high priority testing must wait until the carrier 40 in process is complete. At this point, the completed carrier 40 may be unloaded, the stat sample will be loaded and processed immediately. However, if only one carrier 40 is on the positioner 80, the stat carrier may be loaded immediately and after the current sample is completed, the stat carrier will be positioned for aspiration. Aspiration will resume on the remaining routine samples after all the tube samples on the stat carrier are aspirated.

The computer software includes a preprogrammed priority order for processing samples. For example, the carriers can be selected for processing according to the following priority: 1-unload completed carriers; 2-move aspirated carriers to the loading rack; 3-stat retests; 4-stat tests; 5-stat carrier pick, scan and move to holding area; 6-routine retests; 7-routine tests; 8-routine carrier pick, scan & move to holding area. This ordering of sample priorities has been shown to result in rapid response to high priority samples and maintaining high system throughput. It is understood by one skilled in the art that other priority schemes may be implemented to achieve different levels of performance and responsiveness.

Figure 3:
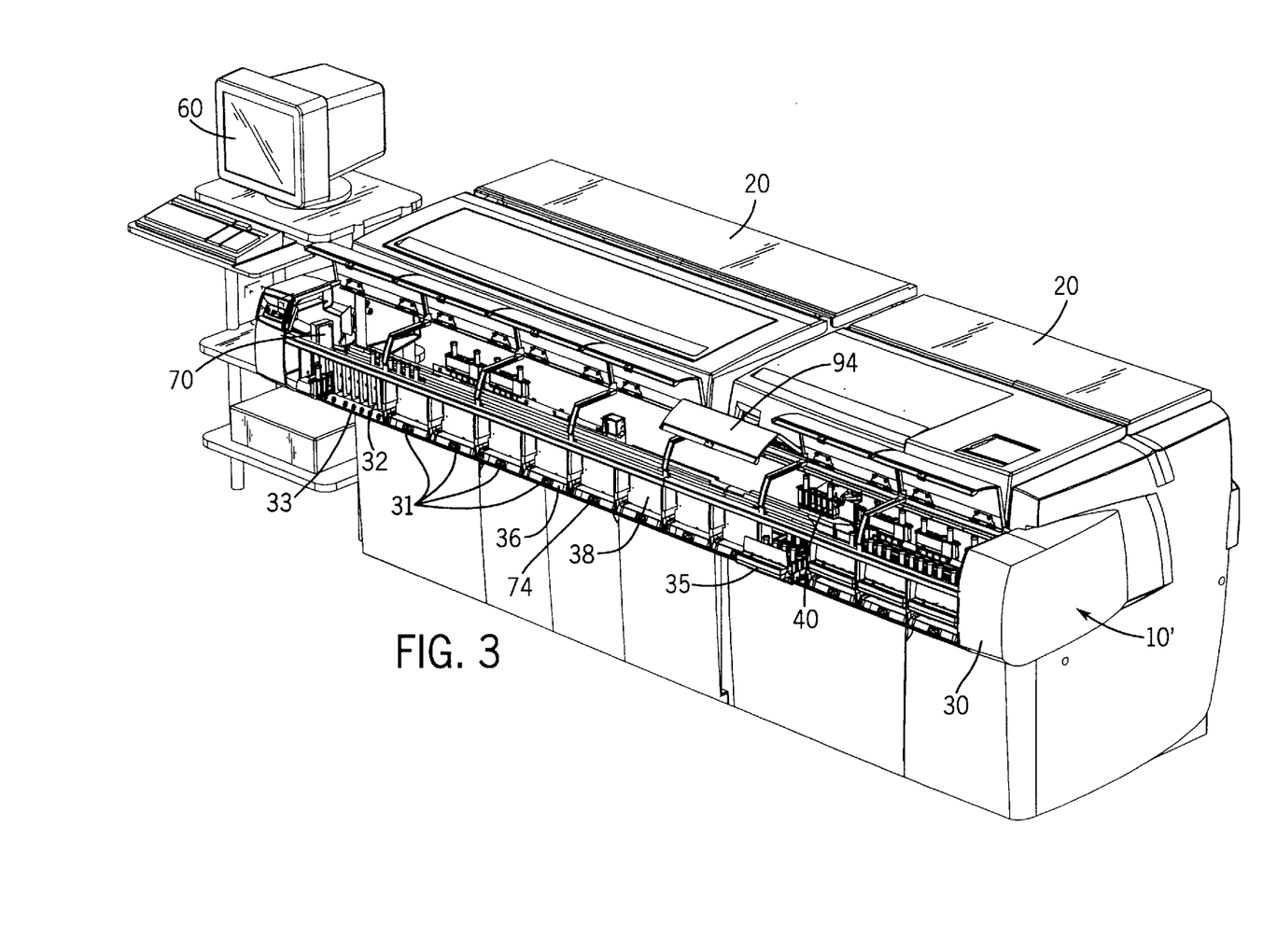
FIG. 3 is a perspective view of a preferred embodiment of the sampling handling system with two diagnostic modules.
Figure 4:
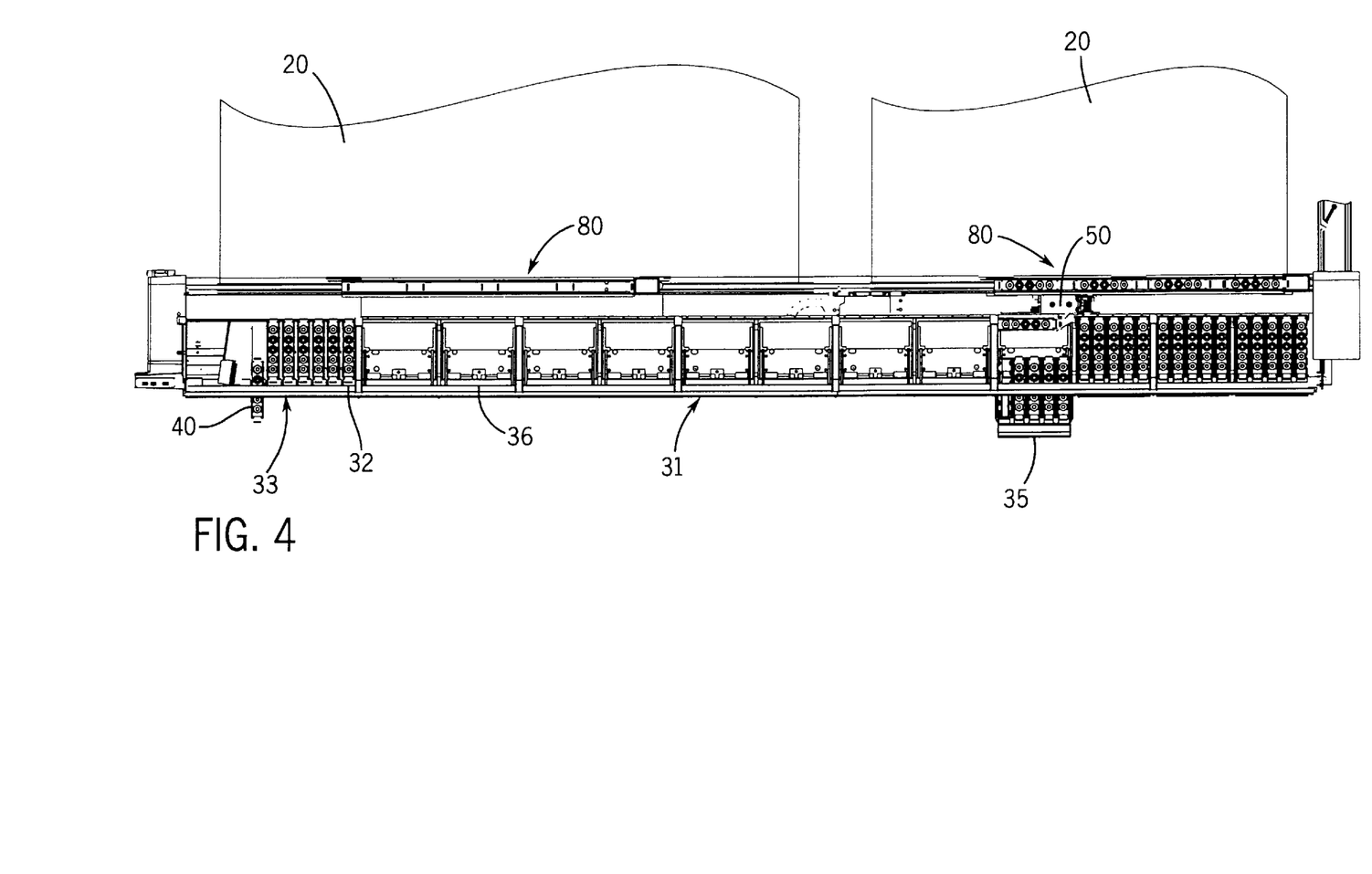
FIG. 4 is a top plan view of the sample handling system of FIG. 3 with access doors removed.

Another preferred embodiment of the sample handling system is shown in FIGS. 3 and 4 with a plurality of diagnostic modules 20. This alternative embodiment is very similar to that depicted in FIGS. 1 and 2. Accordingly, like numerals in FIGS. 3 and 4 indicate the same elements as defined in connection with FIGS. 1 and 2.

The sample handling system 10' in FIGS. 3 and 4 includes at least two diagnostic modules. The diagnostic modules 20 could include immunoassay, clinical chemistry, hematology, or other known diagnostic modules, or a combination of these modules. A carrier positioner 80 is provided for each diagnostic module 20. A sample handling system 10' with a plurality of diagnostic modules 20 enhances the productivity in a lab. Further a multiple module system reduces the requirement to separate or aliquot samples for distribution to different systems. In the present system, samples can be tested with the different modules without removing them from the system. This multiple module system also reduces the space requirements in a lab and can lower the costs of operation.

As shown in FIG. 3, a preferred embodiment of the sample handler system 10' includes a loading rack 30 having seven urgent carrier slots 32 and 12 bays 36 for receiving routine trays 35 holding five carriers 40 each.

Only one carrier transporter 50 and barcode reader 70 are required for the present system, regardless of size. Appropriate control software is required for the present system to select carriers 40 for testing and retesting based on a predetermined priority, direct the operation of the mechanisms, and monitor the system for correct operation.

The present sample handling system is modular and scalable to different sizes of processing modules and may be used for single and dual module system. The system provides random access to sample carriers in the loading platform. This random access capability allows the system to access and process high priority samples rapidly. This capability also allows the system to balance the workload of two processing modules with different throughput capabilities. After samples are processed initially, the samples can be returned to the loading platform and then accessed again when the initial testing is complete to provide automated retest capability. This automated retest capability does not require any additional intervention by the operator. Random access assures the samples to be retested can be processed in the shortest possible time. The system is mechanically simple, which minimizes system cost and maximizes system reliability. The present system is self-contained and can be assembled and tested independently of the processing modules for ease of manufacture and installation in the field.

Several features are included in the present sample handling system to prevent incorrect carrier placement. First, the second and third sensors 104 and 106 on the transporter 50 verify correct alignment of the carrier 40 with the linear positioner 80 and the loading rack 30 respectively. In addition, the first sensor 102 verifies the presence of a carrier 40 on the loading rack 30 and the fourth sensor 107 (not shown) verifies the presence of a carrier 40 on the positioner 80. Further, the system includes frequent software verification of the operation of the sensors.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art.

What is claimed is:

1. A sample handling device for handling a plurality of samples to be tested by a diagnostic module, the sample handling device comprising:
   a plurality of containers, each container adapted for containing a sample;
   a plurality of carriers for holding at least one of the plurality of containers;
   a loading rack for holding the plurality of carriers;
   a positioner adjacent a diagnostic module, the positioner having a plurality of openings adapted for receiving at least one of the plurality of carriers;

a transporter for transporting at least one of the plurality of carriers from the loading rack to the positioner and then back to the loading rack, said transporter having random-access to the plurality of carriers, wherein the positioner receives the carrier and moves the carrier such that the diagnostic module can test at least one of a plurality of samples in the carrier.

2. The sample handling device of claim 1 further comprising a programmable computer for controlling the movement of the transporter and the positioner based on input data and a preprogrammed priority order for processing a plurality of samples.

3. The sample handling device of claim 2 wherein the loading rack includes an urgent sample area for receiving at least one urgent sample carrier, the urgent sample carrier holding at least one urgent sample container adapted for containing an urgent sample.

4. The sample handling device of claim 2, wherein the programmable computer automatically controls the transporter to select a carrier for retesting based on the input data and the preprogrammed priority order for processing samples.

5. The sample handling device of claim 1, wherein the plurality of carriers have a uniquely identifying machine readable label which by reference to the data held by the programmable computer will indicate the tests to be conducted on the samples in the carrier.

6. The sample handling device of claim 1, wherein the transporter comprises a robotic device.

7. The sample handling device of claim 6, wherein the carrier includes a support tab and the robotic device includes a gripping means for gripping to the support tab of the carrier to transport the carrier.

8. The sample handling device of claim 1 wherein the loading rack is configured such that the plurality of carriers are aligned linearly adjacent a diagnostic module.

9. A sample handling device for handling a plurality of samples to be tested by at least one diagnostic module, the sample handling device comprising:
  a loading rack adapted for receiving a plurality of carriers, each carrier adapted to hold at least one of a plurality of samples;
  a positioner adjacent at least one diagnostic module, the positioner having a plurality of openings for receiving at least one of the plurality of carriers;
  a transporter for transporting at least one of the plurality of carriers from the loading rack to the positioner and then back to the loading rack, wherein the positioner moves the carrier such that the diagnostic module can test at least one of a plurality of samples in the carrier; and
  a preprogrammed computer for controlling the movement of the transporter and the positioner based on input data and priority order for processing a plurality of samples.

10. The sample handling device of claim 9 wherein the loading rack includes an urgent sample area for receiving at least one urgent sample carrier, the urgent sample carrier adapted for holding at least one of a plurality of samples.

11. The sample handling device of claim 9, wherein the programmable computer automatically controls the transporter to select a carrier for retesting as required.

12. The sample handling device of claim 9, wherein the plurality of carriers have a uniquely identifying machine readable label which by reference to the data held by the programmable computer will indicate the tests to be conducted on the samples in the carrier.

13. The sample handling device of claim 9, wherein the transporter includes a robotic arm for transporting the plurality of carriers.

14. The sample handling device of claim 13, wherein the carrier includes a support tab and the robotic arm includes a gripping means for gripping to the support tab of the carrier to transport the carrier.

15. A sample handling device for handling samples to be tested by a plurality of diagnostic modules, the sample handling device comprising:
  a plurality of containers, each container adapted for containing a plurality of samples;
  a plurality of carriers for holding at least one of the plurality of containers;
  a loading rack for holding the plurality of carriers;
  a plurality of positioners, each positioner having a plurality of openings for receiving at least one of the plurality of carriers, wherein each diagnostic module has at least one adjacent positioner;
  a transporter for transporting at least one of the plurality carriers between the loading rack and the positioner, the transporter having random-access to the plurality of carriers, wherein the positioner moves the carrier such that the adjacent diagnostic module can test at least one of a plurality of samples in the carrier.

16. The sample handling device of claim 15 further comprising a programmable computer for controlling the movement of the transporter and the positioner based on input data and a preprogrammed priority order for processing the plurality of samples.

17. The sample handling device of claim 16 wherein the loading rack includes an urgent sample area for receiving urgent sample carriers, the urgent sample carriers adapted for holding at least one urgent sample.

18. The sample handling device of claim 17, wherein the programmable computer automatically controls the transporter to select a carrier for retesting as required.

19. The sample handling device of claim 15, wherein the plurality of carriers have a uniquely identifying machine readable label which by reference to the data held by the programmable computer will indicate the tests to be conducted on the samples in the carrier.

20. The sample handling device of claim 15, wherein the transporter comprises a robotic arm for holding each of the plurality of carriers individually.

* * * * *